(12) United States Patent
Chandler et al.

(10) Patent No.: US 6,334,861 B1
(45) Date of Patent: Jan. 1, 2002

(54) BIOPOLAR INSTRUMENT FOR VESSEL SEALING

(75) Inventors: James Gilbert Chandler, Boulder; Randel Alven Frazier, Louisville, both of CO (US)

(73) Assignee: Sherwood Services AG, Schaffhausen (CH)

(*) Notice: Subject to any disclaimer, the term of this patent is extended or adjusted under 35 U.S.C. 154(b) by 0 days.

(21) Appl. No.: 09/376,779

(22) Filed: Aug. 17, 1999

Related U.S. Application Data

(63) Continuation of application No. 08/926,869, filed on Sep. 10, 1997.

(51) Int. Cl.$^7$ .................................................. A61B 18/18
(52) U.S. Cl. ............................ 606/50; 606/45; 606/48; 606/51
(58) Field of Search ..................................... 606/41–52

(56) References Cited

U.S. PATENT DOCUMENTS

| | | |
|---|---|---|
| 371,664 A | 10/1887 | Brannan et al. |
| 702,472 A | 6/1902 | Pignolet |

(List continued on next page.)

FOREIGN PATENT DOCUMENTS

| | | |
|---|---|---|
| EP | 0 584 787 A1 | 3/1994 |
| EP | 0 853 922 A1 | 7/1998 |
| SU | 401367 | 11/1974 |

OTHER PUBLICATIONS

Sigel et al., "The Mechanism of Blood Vessel Closure by High Frequency Electrocoagulation", Surgery Gynecology & Obstetrics, Oct. 1965 pp. 823–831.

(List continued on next page.)

*Primary Examiner*—John Mulcahy
*Assistant Examiner*—David M. Ruddy

(57) ABSTRACT

A bipolar instrument for use by a surgeon to seal tissue with bipolar electrosurgery. The bipolar instrument is a modified hemostat including two elongate members. Each elongate member has a proximal end to be held by a surgeon and a distal end. The elongate members substantially defining a plane and are electrically conductive for transmitting high frequency electrosurgery. A pivot transverse to the plane connects the two elongate members for scissors-like motion between the distal ends. A first tissue contacting pole integral with one elongate member and positioned at its distal end is electrically conductive for transmitting high frequency electrosurgery. Latching elements extend from each elongate member for cooperative interengagement with opposed ramps and abutting stops for sliding conjugation to hold the first and second tissue contacting poles with a predetermined force. An insulated over shoe for placement on the other elongate member at its distal end attaches with a slip fit to prevent longitudinal or transverse movement. That distal end has a reduced cross section for receiving the insulated over shoe in an opening extending thereinto in tunnel fashion. The insulating over shoe has clips for engagement with and about the other elongate member. A second tissue contacting pole affixed to the insulated over shoe and disposed in mirror relationship to the first tissue contacting pole. Two electrical terminals located proximal relative to the pivot to receive bipolar electrosurgery from a source. A first conductor between one terminal and the first tissue contacting pole and a second conductor between the other terminal and the second tissue contacting pole pass bipolar electrosurgery. A switch interrupts continuity in the second conductor for controlled electrosurgery. The switch is atop the pivot in position for surgeon control. A method of assembling the bipolar instrument has the steps of slipping the insulated over shoe onto the other elongate member at its distal end, and attaching the insulated over shoe to the elongate member to prevent longitudinal or transverse movement between the insulated over shoe, the elongate member and the other elongate member.

11 Claims, 6 Drawing Sheets

U.S. PATENT DOCUMENTS

| | | | |
|---|---|---|---|
| 728,883 A | 5/1903 | Downes |
| 1,586,645 A | 6/1926 | Bierman |
| 2,002,594 A | 5/1935 | Wappler et al. |
| 2,176,479 A | 10/1939 | Willis |
| 3,643,663 A | 2/1972 | Sutter |
| 3,651,811 A | 3/1972 | Hildebrandt et al. |
| 3,920,021 A | 11/1975 | Hiltebrandt |
| 3,938,527 A | 2/1976 | Rioux et al. |
| 3,952,749 A | 4/1976 | Fridolph et al. |
| 4,005,714 A | 2/1977 | Hiltebrandt |
| 4,370,980 A | 2/1983 | Lottick |
| 4,552,143 A | 11/1985 | Lottick |
| 4,597,379 A | 7/1986 | Kihn et al. |
| 4,671,274 A | 6/1987 | Sorochenko |
| 4,685,459 A | 8/1987 | Koch et al. |
| 4,887,612 A | 12/1989 | Esser et al. |
| 4,938,761 A | 7/1990 | Ensslin |
| 5,026,370 A | 6/1991 | Lottick |
| 5,116,332 A | 5/1992 | Lottick |
| 5,151,102 A | 9/1992 | Kamiyama et al. |
| 5,176,695 A | 1/1993 | Dublebohn |
| 5,217,458 A | 6/1993 | Parins |
| 5,250,047 A | 10/1993 | Rydell |
| 5,258,006 A | 11/1993 | Rydell et al. |
| 5,277,201 A | 1/1994 | Stern |
| 5,324,289 A | 6/1994 | Eggers |
| 5,330,471 A | 7/1994 | Eggers |
| 5,342,359 A | 8/1994 | Rydell |
| 5,352,222 A | 10/1994 | Rydell |
| 5,356,408 A | 10/1994 | Rydell |
| 5,389,104 A | 2/1995 | Hahnen et al. |
| 5,391,166 A | 2/1995 | Eggers |
| 5,403,312 A | 4/1995 | Yates et al. |
| 5,431,674 A | 7/1995 | Basile et al. |
| 5,443,463 A | 8/1995 | Stern et al. |
| 5,443,464 A | 8/1995 | Russell et al. |
| 5,445,658 A | 8/1995 | Durrfeld et al. |
| 5,456,684 A | 10/1995 | Schmidt et al. |
| 5,462,546 A | 10/1995 | Rydell |
| 5,472,443 A | 12/1995 | Cordis et al. |
| 5,478,351 A | 12/1995 | Meade et al. |
| 5,484,436 A | 1/1996 | Eggers et al. |
| 5,509,922 A | 4/1996 | Aranyi et al. |
| 5,527,313 A | 6/1996 | Scott et al. |
| 5,531,744 A | 7/1996 | Nardella et al. |
| 5,540,684 A | 7/1996 | Hassler, Jr. |
| 5,558,672 A | 9/1996 | Edwards et al. |
| 5,569,241 A | 10/1996 | Edwards |
| 5,573,535 A | 11/1996 | Viklund |
| 5,626,578 A | 5/1997 | Tihon |
| 5,637,110 A | 6/1997 | Pennybacker et al. |
| 5,658,281 A | 8/1997 | Heard |
| 5,667,526 A | 9/1997 | Levin |
| 5,674,220 A | 10/1997 | Fox et al. |
| 5,693,051 A | 12/1997 | Schulze et al. |
| 5,700,261 A | 12/1997 | Brinkerhoff |
| 5,702,390 A | 12/1997 | Austin et al. |
| 5,766,166 A | 6/1998 | Hooven |
| 5,769,849 A | 6/1998 | Eggers |
| 5,776,128 A | 7/1998 | Eggers |
| 5,776,130 A | 7/1998 | Buysse et al. |
| 5,792,137 A | * 8/1998 | Carr et al. ..................... 606/29 |
| 5,827,281 A | 10/1998 | Levin |
| 5,951,549 A | * 9/1999 | Richardson et al. .......... 606/45 |
| 6,024,741 A | * 2/2000 | Williamson, IV et al. .... 606/40 |
| 6,024,744 A | * 2/2000 | Kese et al. ................... 606/51 |
| 6,050,996 A | 4/2000 | Schmaltz et al. |

OTHER PUBLICATIONS

Bergdahl et al. "Studies on Coagulation and the Development of an Automatic Computerized Bipolar Coagulator", J. Neurosurg, vol. 75, Jul. 1991, pp. 148–151.

International Search Report—PCT/US98/18640.

International Search Report—PCT/US98/23950.

International Search Report PCT/US99/24869.

* cited by examiner

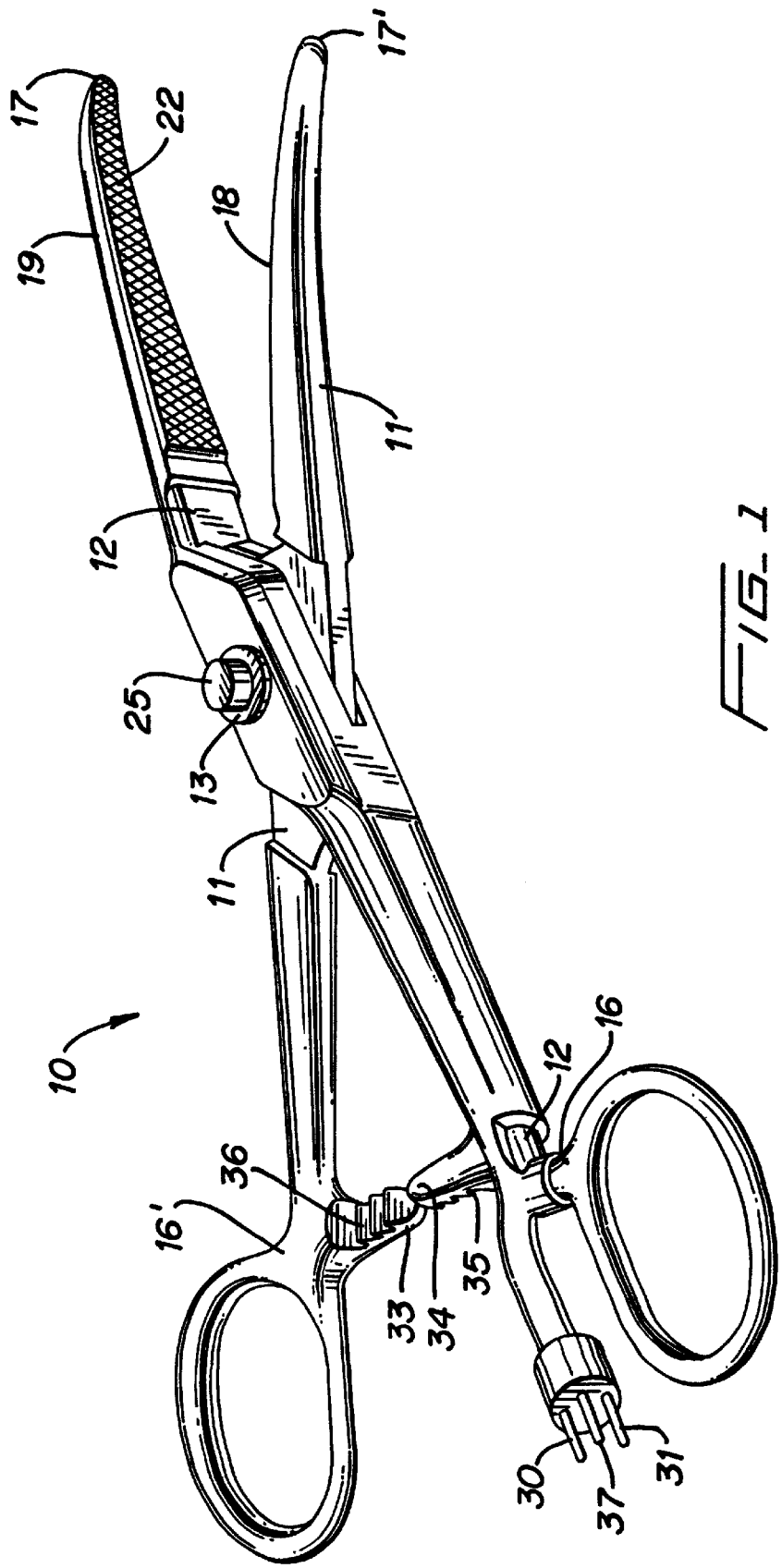

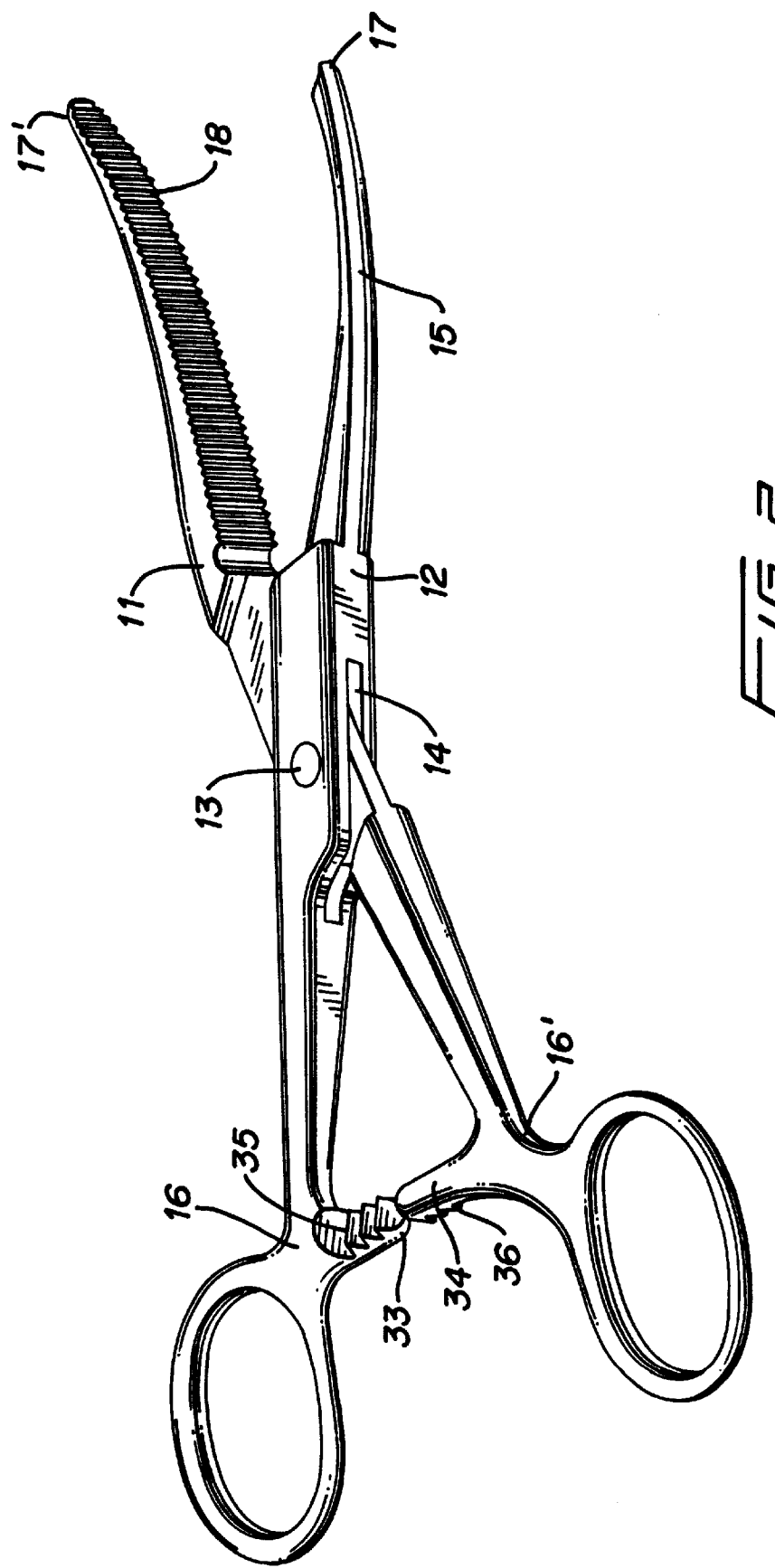

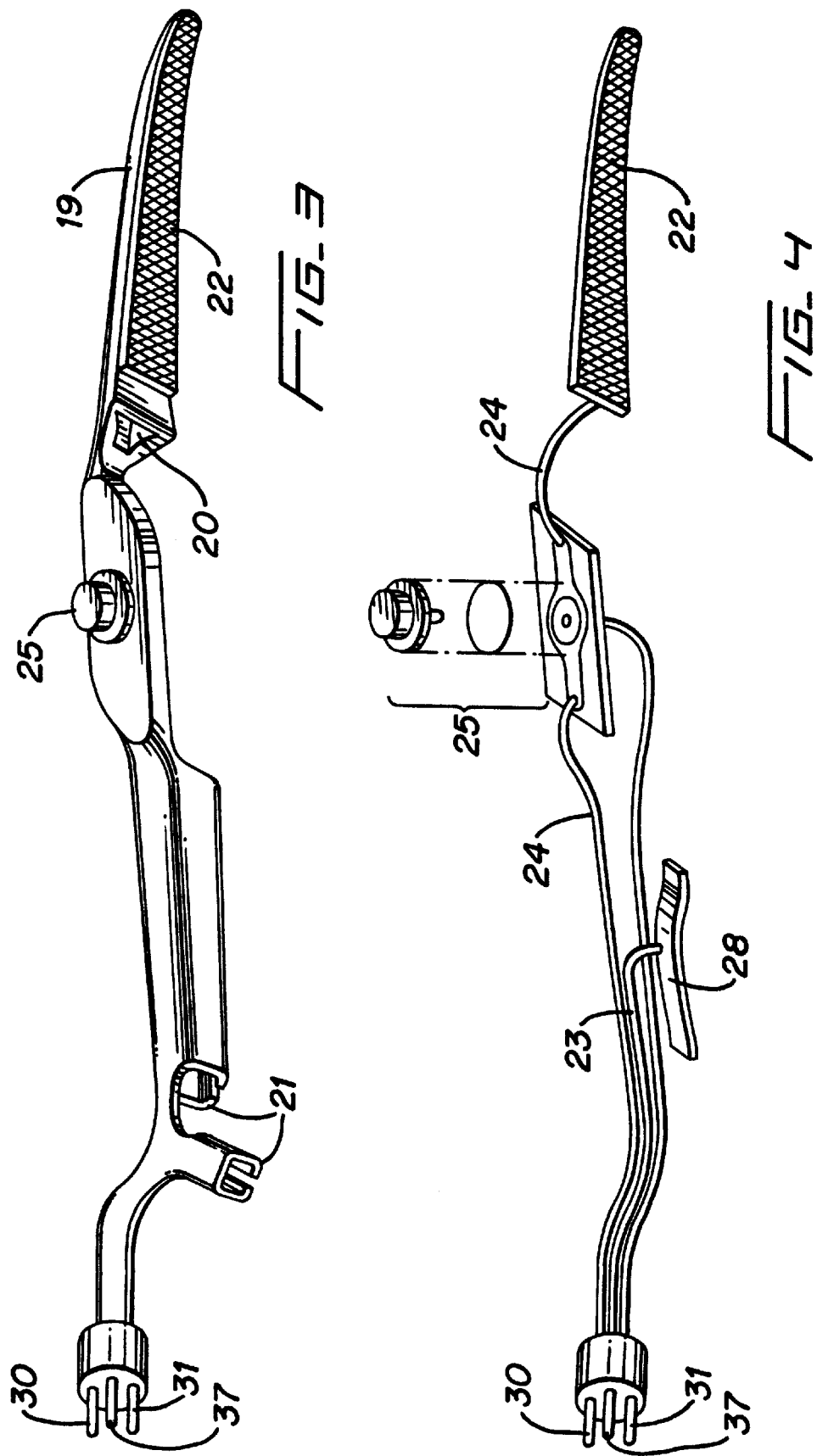

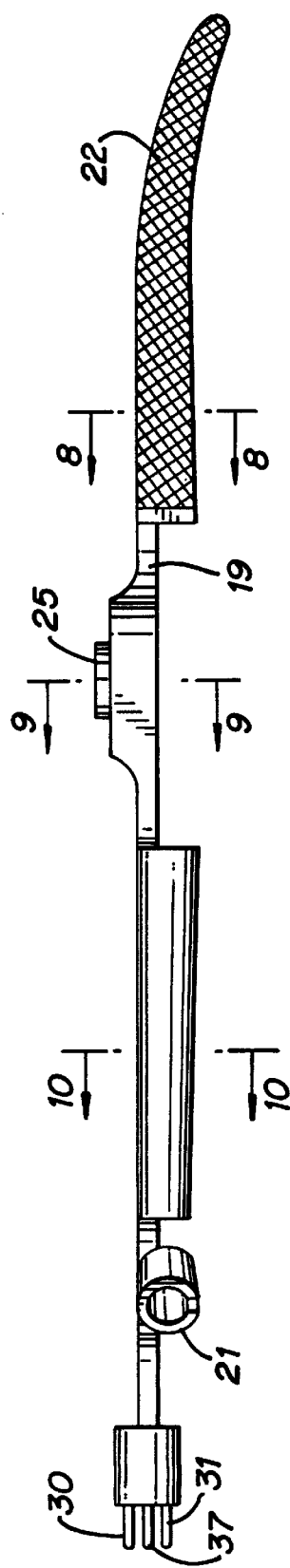
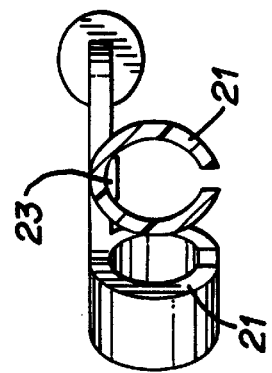
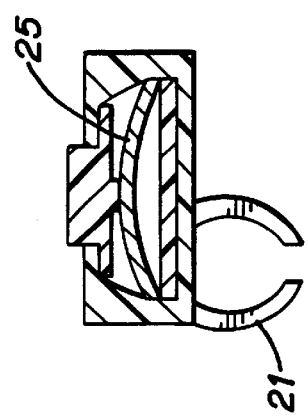
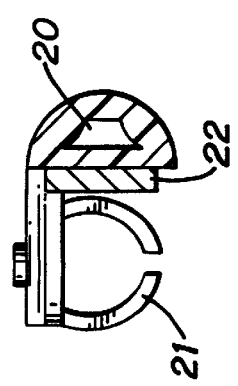
FIG. 7
FIG. 10
FIG. 9
FIG. 8

BIOPOLAR INSTRUMENT FOR VESSEL SEALING

This application is a continuation of U.S. application Ser. No. 08/926,869 filed on Sep. 10, 1997, the contents of which are hereby incorporated by reference in their entirety.

FIELD OF THE INVENTION

This invention relates to a surgical instrument for permanently closing vessels in a human or animal, and more particularly to a modified hemostat that fuses vessel tissue using a combination of pressure and electrosurgical current.

BACKGROUND OF THE DISCLOSURE

A hemostat is commonly used in surgical procedures to close off veins and arteries. It is typically a simple pliers-like tool that uses mechanical action between its jaws to constrict a vessel without cutting it. It is also typical to have an interlocking ratchet between the handles so that the device can be clamped and locked in place.

Many hemostats are used in a typical open surgical procedure. Once a structure has been clamped, it is common for a surgeon to tie a suture around the structure to close it off permanently prior to removing the hemostat. Several hemostats may be left in the surgical field until the surgeon has the opportunity to tie them all off. It would be desirable for surgeons the fuse the vessels immediately, and thus avoid having hemostats obstructing access to the surgical site.

A number of bipolar electrosurgical forceps and clamps are known in the field.

All of these designs suffer from the drawback that they do not combine the simplicity and familiarity of a hemostat with bipolar electrosurgery. For example, U.S. Pat. No. 5,462,546 discloses bipolar electrosurgical forceps comprising two interfacing pivotal blade members which are individually pivotable in relation to each other. Pivotal movement of the members is effectuated by two electrically conductive rigid rods extending through an elongated tubular member.

A U.S. Patent application entitled, Energy Delivery System for Vessel Sealing, Ser. No. 08/530,495, filed Sep. 19, 1995, discloses an apparatus and method for vessel sealing, and is hereby incorporated by reference and made a part of this disclosure.

A U.S. Patent application entitled, Vascular Tissue Sealing Pressure Control and Method, Ser. No. 08/530,450, filed Sep. 19, 1995, discloses a surgical tool for sealing vessels, and is hereby incorporated by reference and made a part of this disclosure.

U.S. Pat. No. 5,116,332 to Lottick discloses an electrocautery hemostat. The hemostat includes clam-shell type synthetic plastic handles with a switch incorporated therein.

U.S. Pat. No. 5,026,370 to Lottick discloses an electrocautery instrument with a non-removable enclosed electrical switching mechanism. U.S. Pat. No. 4,370,980 discloses an electrocautery instrument which may be used as a clamping device and an apparatus for cauterizing bleeding blood vessels during surgery.

U.S. Pat. No. 5,484,436 to Eggers discloses bipolar electrosurgical instruments. The bipolar instruments include opposite polarity electrodes isolated by a layer of electrical insulation deposited and specially prepared to reduce electrical breakdown and increase smoothness.

U.S. Pat. No. 5,443,464 to Stern et al. discloses a coagulating forceps having a plurality of electrodes and sensors on the jaws. The sensors provide a feedback signal to an electrosurgical generator in order to control the amount of heat in the forceps.

U.S. Pat. No. 4,005,714 to Hiltebrandt discloses bipolar coagulation forceps in which the forceps are designed to coagulate both the fallopian tube and the adjacent mesosalpinx.

SUMMARY OF THE INVENTION

It is the general objective of this invention to provide an instrument that can fuse structures without the need for a suture. The instrument has electrosurgical current flowing between the working jaws. The electrosurgical current passes through the clamped structure and forms a permanent seal.

One advantage of the invention is that blood vessels can be more quickly fused than with standard instruments.

Another advantage is that no sutures are required to permanently seal blood vessels.

Yet another advantage is that vessels can be sealed as the instrument is applied, and then the instrument can be removed from the surgical field. This keeps the surgical field clear of extraneous tools that may hinder the surgeon's access to the surgical site.

The ability of the bipolar instrument to seal tissue partly depends on two elements: the pressure exerted on the vessel as it is grasped between the tissue contacting surfaces, and the characteristics of the bipolar electrosurgical energy which is conducted through the vessel. The pressure exerted on the vessel depends on the force exerted between the tissue contacting surfaces, and also on the cross sectional area of the tissue being grasped. It has been found through experimentation that a desirable force between the tissue contacting surfaces is less for ligating veins than for ligating arteries. It is desirable to avoid closure forces which cause the tissue to split or separate.

The characteristics of the bipolar electrosurgical energy are determined by the design of the electrosurgical generator. The bipolar instrument, described herein, is designed to be electrically connected to an electrosurgical generator with bipolar output.

BRIEF DESCRIPTION OF THE DRAWINGS

FIG. 1 is a perspective view of the bipolar modified hemostat for delivering electrosurgery.

FIG. 2 is a perspective view of the modified hemostat of FIG. 1 without an insulating over shoe in place, showing one of the elongate members having a reduced cross section distal end.

FIG. 3 is a perspective view of the insulating over shoe as it would appear from above.

FIG. 4 is an exploded view of the wiring for the switch portion of the insulated over shoe, with the insulation and support portion thereof removed.

FIG. 7 is a side elevation view of the insulated over shoe of FIG. 3.

FIG. 8 is a view in cross section of the insulated over shoe of FIG. 7 as would be seen along lines; 8—8 thereof.

FIG. 9 is a view in cross section of the insulated over shoe of FIG. 7 as would be seen along lines 9—9 thereof FIG. 10 is a view in cross section of the insulated over shoe of FIG. 7 as would be seen along lines 10—10 thereof.

DETAILED DESCRIPTION OF THE INVENTION

Figure 5:
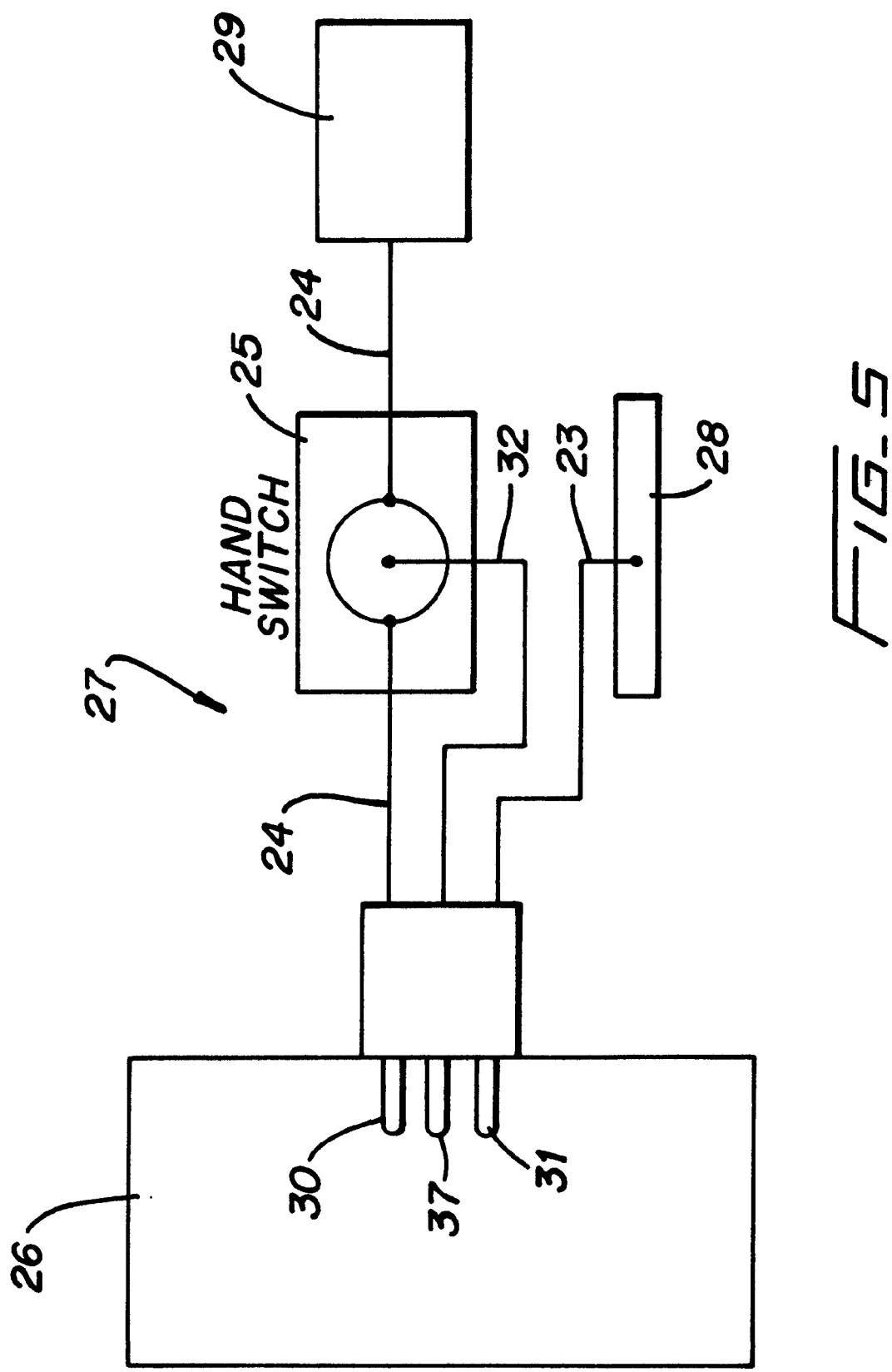
FIG. 5 is a circuit diagram for the switch shown in FIG. 4.

In the preferred embodiment of a bipolar instrument, each of the elongate members 11 and 12 is formed from an electrically conductive material. A pivot 13 connects the two elongate members 11 and 12 in a manner that provides for scissors-like motion as in a modified hemostat 15. The pivot 13 may be a simple pin, as in FIGS. 1 and 2, or it may be an integral part of a lock box assembly 14. FIG. 1 shows the bipolar instrument 10 in a top perspective view and FIG. 2 shows the modified hemostat 15 in a bottom perspective view. In a well known manner, the pivot 13 can be electrically insulated to prevent flow of electrosurgical current from one of the elongate members either 11 or 12 to the other. In the preferred embodiment, the pivot 13 is uninsulated because it is not a potential path between the two poles of bipolar electrosurgical energy. The modified hemostat 15 of the bipolar instrument 10 is made very much like a standard hemostat and can be used for bipolar electrosurgery and can be sterilized just as a standard hemostat. It is the disclosed invention that allows the conversion of a standard hemostat to use with bipolar electrosurgery. FIG. 1 is a perspective view of the bipolar instrument 10 based on the modified hemostat 15 shown in FIG. 2 so that bipolar electrosurgery can be delivered.

The bipolar instrument 10, as the modified hemostat 15 in FIG. 2 may include two elongate members 11 and 12. Each elongate member either 11 or 12 preferably has a proximal end 16 or 16' to be held by the surgeon and a distal end 17 or 17' for manipulation of tissue or vasculature. In the figures and throughout this description the proximal end 16' on the one elongate member 11 will be referred to as 16' and the distal end 17' on the one elongate member 11 will be called 17'. Similarly, the proximal end 16 on the other elongate member 12 will be referred to as 16 and the distal end 17 on the other elongate member 12 will be called 17. The proximal end 16 or 16' may have features that make it easy for the surgeon to grasp, such as loops for the surgeon's fingers.

A first tissue contacting pole 18 is integral with one elongate member 11 and located on one distal end 17', as best seen in FIG. 2. The first tissue contacting pole 18 is preferably integral with the one elongate member 11 which is preferably made of an electrically conductive material such as stainless steel or aluminum so that it can conduct bipolar electrosurgery.

The bipolar instrument 10 has an insulated over shoe 19 for placement on the other elongate member 12 at its distal end 17. The insulating over shoe 19 attaches to the other elongate member 12 in slip fit relation about the other distal end 17 to prevent longitudinal or transverse movement between the insulated over shoe 19, the other elongate member 12 and the other distal end 17. FIG. 2 is a perspective view of the modified hemostat of FIG. 1 without the insulating over shoe 19 in place, showing other elongate member 12 having a reduced cross section at distal end 17. The distal end 17 has a reduced cross section for receiving the insulated over shoe 19 in a slip fit relationship. FIG. 3 is a perspective view of the insulating over shoe 19 as it would appear from above. Consequently, the insulating over shoe 19 includes an opening 20 extending thereinto in tunnel fashion for slip fit relation over the reduced cross section of the distal end 17. Thus longitudinal or transverse movement between the insulated over shoe 19, the other elongate member 12 and its distal end' 17 are prevented. The insulating over shoe 19 has clips 21 for engagement with and about the other elongate member 12. The insulated over shoe 19 is designed to carry circuitry for conducting the bipolar electrosurgical energy along the other elongate member 12 to its respective second tissue contacting pole 22. Specifically, the second tissue contacting pole 22 is on the insulated over shoe 19 is position to oppose the first tissue contacting pole 18 so that placement of the insulated over shoe 19 on the other distal end 17 will cause precise alignment of the first and second tissue contacting poles 18 and 22 across from one another. The first and second tissue contacting poles 18 and 22 are connected to first and second conductors 23 and 24, respectively as best understood from FIGS. 4 and 5.

Figure 6:
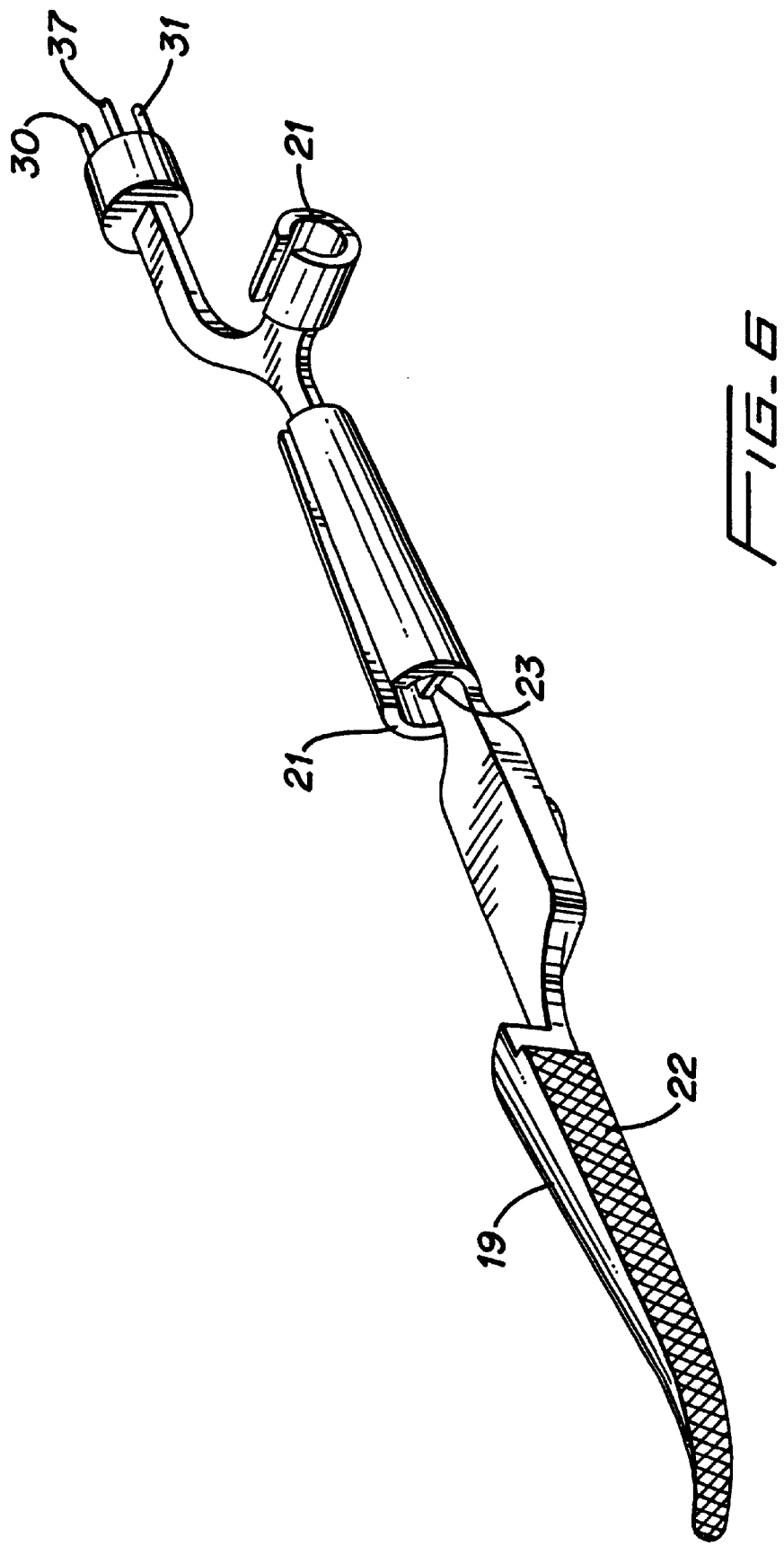
FIG. 6 is a perspective view of the insulated over shoe as it would appear from beneath.

A switch 25 best shown in FIGS. 4 and 5, the latter schematically, interrupts the continuity of the second conductor 24 between the second tissue contacting pole 22 and a source of bipolar electrosurgery 26. A preferred source of bipolar electrosurgery 26 is made by Valleylab Inc of Boulder, Colo., the assignee of this invention; specifically, the Force FX electrosurgical generator that has a bipolar output. As shown in the schematic diagram of FIG. 5 there is a circuit 27 between the source of bipolar electrosurgery 26 and contact plates 28 and 29. Contact plates 28 and 29 are also shown in FIG. 5 wherein the contact plate 28 is merely to transfer electrosurgery to the modified hemostat 15 by intimate pressure contact. Similarly the contact plate 29 is equivalent to the second tissue contacting pole 22 in the preferred embodiment; skilled artisans will know that the contact plate 29 and the second tissue contacting pole 22 can be separate items that are electrically coupled by perhaps the assembly of the insulated over shoe 19 onto the other distal end 17. Terminals 30 and 31 are shown in FIGS. 3, 4, 5, 6 and 7 to detachably and easily electrically couple the source of bipolar electrosurgery 26 to the bipolar instrument 10 and more particularly, the conductors 24 and 23, respectively as best understood from FIG. 5 attach to terminals 30 and 31. Contact plate 28 is thus connected directly by first conductor 23 to terminal 31 while second conductor 24 is connected between terminal 30 and the switch 25. The other side of the switch 25 is directly electrically coupled to the second tissue contacting pole 22 by the continuation of first conductor 24 in the preferred embodiment. Terminals 30 and 31 attach to the bipolar output of the source of bipolar electrosurgery 26; that is both sides of the bipolar output. Switch 25, in FIG. 5 includes a hand switch control 32 to activate the source of bipolar electrosurgery 26 to supply bipolar output as required by the surgeon. Thus, when the switch 25 is closed bipolar electrosurgery output is received at the terminals 30 and 31 for controlled selective passage of bipolar electrosurgery from the first tissue contacting pole 18 to the second tissue contacting pole 22. Switch 25 is preferably disposed atop the pivot 13 in a convenient position for the surgeon to control the flow of electrosurgery. FIG. 4 is an exploded view of the wiring for the switch 25 of the insulated over shoe and FIG. 5 is a circuit diagram for the switch 25 shown in FIG. 4. FIG. 6 is a perspective view of the insulated overshoe 19 as it would appear from beneath. The modified hemostat 15 and its elongate members 11 and 12 are constructed from an electrically conductive material, such as stainless steel or aluminum. Consequently bipolar electrosurgery will pass through tissue between the first and second contacting poles 18 and 22 when tissue is grasped therebetween and the switch 25 is closed.

The bipolar instrument 10 has certain similarities to the look and feel of a standard hemostat so that it will be comfortable and familiar to surgeons. However, the bipolar instrument 10 has the added capability of ligating vessels and sealing vascular tissue. The source of bipolar electrosurgery 26 is electrically connected to the bipolar instrument 10 terminals 30 and 31 to provide bipolar high frequency electrosurgery.

The first and second conductors 23 and 24 are in the preferred embodiment of FIG. 4 shown as insulated wires carried in the insulated over shoe 19 along the other elongate member 12 for carrying electrosurgery current from the terminals 30 and 31. The insulated wires may be press-fit, or are injection molded as part of the insulated over shoe 19. Thus the pivot 13 is not needed be electrically insulated. FIG. 7 is a side elevation view of the insulated over shoe 19 of FIG. 3 showing how compact and thus light weight it is. FIG. 8 is a view in cross section of the insulated overshoe 19 of FIG. 7 as would be seen along lines 8—8 thereof FIG. 9 is a view in cross section of the insulated over shoe of FIG. 7 as would be seen along lines 9—9 thereof FIG. 10 is a view in cross section of the insulated over shoe 19 of FIG. 7 as would be seen along lines 10—10 thereof Clips 21 are best shown in FIGS. 6, 7, 8, 9 and 10 while the insulated over shoe 19 assembled to the modifier hemostat 15 is illustrated in FIG. 1.

An alternative, not shown but familiar to those skilled in design and use of hemostats is to curve the distal ends 17 and 17' more than already shown to extend transverse relative to the plane and generally parallel to but spaced from the pivot 13. Curved hemostats offer access to ease the surgeon's manipulation during certain surgeries. The insulated over shoe 19 should be flexible enough to be easily slid over the reduced cross section distal end 17'. Polymers that have a high dielectric, high temperature resistance and low cost are preferred. Similarly, the switch 25 has a printed circuit board to facilitated its low cost manufacture.

Latching elements 33 and 34 are located on each elongate member 11 and 12 preferably proximal of the pivot 13. Thus in the preferred embodiment these latching elements 33 and 34 are located near the proximal ends 16 and 16' of the bipolar instrument 10, i.e. closer to the finger loops. The latching elements 33 and 34 preferably have opposed ramps 35 and abuttable stops 36 for their well known sliding conjugating engagement. At least three abuttable stops 36 may be provided for yielding successively greater closure forces between the first and second tissue contacting poles 18 and 22. At least one abuttable stop 36 on each elongate member 11 and 12 will yield a small closure force between the first and second tissue contacting poles 18 and 22 for small vessels. At least one other abuttable stop 36 on each elongate member 11 and 12 will yield a great closure force between the first and second tissue contacting poles 18 and 22 for larger vessels. In the preferred embodiment the latching elements 33 and 34 will hold the closure force against the strain energy of the elongate members 11 and 12 which will be slightly deflected by the opposed camming of ramps 35 prior to reaching juxtapositioning of each successive abutting stop 36. This described action is common to any standard hemostat but represents something different in a bipolar hemostat.

The one elongate member 11 is attached to a different electrical polarity in the bipolar electrosurgical circuit 27 than the other elongate member 12 carrying the insulated over shoe 19 at its distal end. Because of the insulated over shoe 19 the pivot 13 need not be electrically insulated so as to prevent an electrical short circuit between the elongate members 11 and 12 since they are at the same polarity in the vicinity of the pivot 13. It is thus possible to use standard hemostat designs and manufacturing techniques to make the modified hemostat 15 of FIG. 2 or the like. Similarly, the latching elements 33 and 34 need not be electrically insulated to prevent an electrical short circuit in the vicinity of the their ramps 35 and abutting stops. This is particularly good as the frictional engagement of the ramps 35 and abutting stops 36 would stress typical dielectric coatings and/or isolation approaches.

The two electrical terminals 30 and 31 are preferably located on toward the surgeon or proximal ends 16 and 16' and preferable on the latter. As explained, the terminals 30 and 31 are supplied by the source of bipolar electrosurgery 26 with opposite polarity. A prong 37 connected to hand switch control 32 is for switching as best shown in FIG. 5. In the preferred embodiment, the terminals are supported on the other elongate member 12 near its proximal end 16. For bipolar instruments which are reusable, the terminals 30 and 31 and the prong 37 are designed to quickly disconnection from the source of bipolar electrosurgery 26 to remove the modified hemostat 15.

A method of assembly of the insulated over shoe 19 and the modified hemostat 15 includes the steps of slipping the insulated over shoe 19 onto the other distal end 17, and then attaching the insulated over shoe 19 to the other elongate member 12 to prevent longitudinal or transverse movement between the insulated over shoe 19, the other elongate member 12 and its other distal end 17.

Ordinarily, available commercial bipolar graspers, clamps and the like are designed to be disposable after each operation or if reusable, each must be sterilized and checked for electrical safety, i.e. leakage. The bipolar instrument 10 disclosed is separable from the electrical components such that the latter need only be disposable, and thus the safety is improved and cost is reduced and the ease of sterilization is assured.

It is to be understood that the described and claimed bipolar instrument 10 is only illustrative of one application of the principles of the present invention. Numerous modifications and alternative arrangements may be devised by those skilled in the art without departing from the spirit and scope of the present invention. The appended claims are intended to cover such modifications and arrangements.

What is claimed is:

1. A bipolar instrument for use by a surgeon to seal tissue with bipolar electrosurgery, the bipolar instrument comprising:

two elongate members, each elongate member having a proximal end to be held by a surgeon and a distal end, the elongate members substantially defining a plane, the elongate members made of at least some electrically conductive material for transmitting high frequency electrosurgery therethrough;

a pivot connecting the two elongate members in a manner that provides for scissors-like motion between the elongate members, the pivot transverse to the plane, the pivot disposed away from the distal ends for allowing transverse motion of the distal ends;

a first tissue contacting pole integral with one elongate member and positioned at its distal end, the first tissue contacting pole electrically conductive for transmitting high frequency electrosurgery;

an insulated over shoe for placement on the other elongate member at its distal end, the insulating over shoe for attachment to the other elongate member in slip fit relation about that distal end to prevent longitudinal or transverse movement between the insulated over shoe, the elongate member and the other distal end;

a second tissue contacting pole affixed onto the insulated over shoe, the second tissue contacting pole disposed in mirror relationship to the first tissue contacting pole;

two electrical terminals located proximal relative to the pivot and configured to receive bipolar electrosurgical energy;

a first conductor between one terminal and the first tissue contacting pole, and a second conductor electrically coupling the other terminal and the second tissue contacting pole for providing a circuit to pass bipolar electrosurgical energy from the first tissue contacting pole to the second tissue contacting pole.

2. The bipolar instrument according to claim 1, wherein latching elements near the proximal ends extend from each elongate member for cooperative interengagement, the latching elements having at least opposed first and second ramps and stops for sliding conjugating for holding the first and second tissue contacting poles with a first or a second predetermined force therebetween.

3. The bipolar instrument according to claim 1, wherein the instrument is a modified hemostat with the pivot for scissors-like motion between the distal ends, the modified hemostat with the distal ends curved to extend transverse relative to the plane and generally parallel to but spaced from the pivot.

4. The bipolar instrument according to claim 3 wherein a switch interrupts the continuity of the second conductor between its terminal so the second tissue contacting pole is controlled to permit selective passage of bipolar electrosurgery between the first tissue contacting pole and the second tissue contacting pole, the switch being disposed atop the pivot in position for the surgeon to control the flow of electrosurgery and a prong located near the terminals connects to the switch to signal the need for electrosurgery.

5. The bipolar instrument according to claim 1, wherein the other member at its distal end has a reduced cross section for receiving the insulated over shoe.

6. The bipolar instrument according to claim 5, wherein the insulating over shoe has an opening extending thereinto in tunnel fashion for slip fit relation of the reduced cross section of the other distal end to prevent longitudinal or transverse movement between the insulated over shoe, the elongate member and the other distal end.

7. The bipolar instrument according to claim 1, wherein the insulating over shoe has clips for engagement with and about the other elongate member.

8. The bipolar instrument according to claim 1, wherein the instrument is a modified hemostat with the pivot between the proximal and distal ends for scissors-like motion of the elongate members between the distal ends.

9. The bipolar instrument according to claim 1 wherein a source of bipolar electrosurgery connects separately to the terminals to supply, respectively bipolar high frequency electrosurgery thereto.

10. A method of assembling a bipolar instrument for use by a surgeon to seal tissue with bipolar electrosurgery, the bipolar instrument including two elongate members, each elongate member having a proximal end to be held by a surgeon and a distal end, the elongate members substantially defining a plane, The elongate members of an electrically conductive material for transmitting high frequency electrosurgery; a pivot connecting the two elongate members in a manner that provides for scissors-like motion between the elongate members, the pivot transverse to the plane, the pivot disposed away from the distal ends for allowing transverse motion of the distal ends; a first tissue contacting pole integral with the one elongate member and positioned at its distal end, the first tissue contacting pole of an electrically conductive material for transmitting high frequency electrosurgery; an insulated over shoe for placement on the other distal end; a second tissue contacting pole affixed to the insulated over shoe, the second tissue contacting pole located for mirror relationship to the first tissue contacting pole; two electrical terminals located proximal relative to the pivot and configured to receive bipolar electrosurgery; a first conductor between one terminal and the first tissue contacting pole, and a second conductor between the other terminal and the second tissue contacting pole for passage of bipolar electrosurgery between the first tissue contacting pole and the second tissue contacting pole, the method of assembly having the steps of:

slipping the insulated over shoe onto the other elongate member at its distal end, and attaching the insulated over shoe to the elongate member to prevent longitudinal or transverse movement between the insulated over shoe, the elongate member and the other elongate member.

11. A bipolar instrument for use by a surgeon to seal tissue with bipolar electrosurgery, the bipolar instrument is a modified hemostat comprising:

two elongate members, each elongate member having a proximal end to be held by a surgeon and a distal end, the elongate members substantially defining a plane, the elongate members electrically conductive for transmitting high frequency electrosurgery;

a pivot connecting the two elongate members in a manner that provides for scissors-like motion between the distal ends and the distal ends are curved to extend transverse relative to the plane and generally parallel to but spaced from the pivot, the pivot transverse to the plane and disposed away from the distal ends for allowing transverse motion of the distal ends.

* * * * *